United States Patent [19]

Teach

[11] 4,269,986
[45] May 26, 1981

[54] HYDROXYACETYL OXAZOLIDINE HERBICIDAL ANTIDOTES

[75] Inventor: Eugene G. Teach, El Cerrito, Calif.

[73] Assignee: Stauffer Chemical Company, Westport, Conn.

[21] Appl. No.: 143,665

[22] Filed: Apr. 25, 1980

[51] Int. Cl.³ .................. C07D 263/04; A01N 43/76
[52] U.S. Cl. ........................................ 548/215; 71/88
[58] Field of Search ........................................ 548/215

[56] References Cited

U.S. PATENT DOCUMENTS

| | | | |
|---|---|---|---|
| 2,250,408 | 7/1941 | De Groote | 548/215 |
| 2,571,985 | 10/1951 | Carnes | 548/215 |
| 4,021,224 | 5/1977 | Pallos et al. | 548/215 |
| 4,072,688 | 2/1978 | Teach | 548/215 |

Primary Examiner—Anton H. Sutto
Attorney, Agent, or Firm—Harry A. Pacini

[57] ABSTRACT

Compounds having the formula

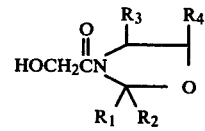

in which $R_1$–$R_4$ are each independently selected from the group consisting of hydrogen and alkyl having 1–4 carbon atoms protect corn from thiolcarbamate herbicidal injury.

2 Claims, No Drawings

HYDROXYACETYL OXAZOLIDINE HERBICIDAL ANTIDOTES

BACKGROUND OF THE INVENTION

Uses of Herbicides

A herbicide is a compound which controls or modifies plant growth, e.g., killing, retarding, defoliating, desiccating, regulating, stunting, tillering, stimulating, dwarfing and the like. "Plant" refers to all physical parts, including seeds, seedlings, saplings, roots, tubers, stems, stalks, foliage and fruits. "Plant growth" is meant to include all phases of development from seed germination to natural or induced cessation or life.

Herbicides are generally used to control or eradicate weed pests. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the beneficial crop and selectivity toward weeds. Certain herbicidal compounds are phytotoxic to some weed species but not to others.

A manufacturer of a herbicide generally recommends a range of rates and concentrations calculated to maximize weed control. The range of rates usually varies from approximately 0.1 to approximately 50 pounds per acre (lb/A) [0.112 to 58 kilograms per hectare (k/ha)], usually from 0.1 to 25 lb/A (0.112 to 26 k/ha). The actual amount used depends upon several considerations, including, crop tolerance, particular weed susceptibility and overall cost limitations.

Some herbicides display exclusive selectivity toward weed species. Many are toxic to both weeds and the intended crop beneficiary. Therefore, a particular herbicide may proscribe its injurious effect on the cultivated crop even though it may otherwise provide excellent control of weeds found in the crop field.

To preserve the beneficial aspects of herbicide use and to mitigate crop damage, many herbicidal antidotes have been prepared. These antidotes reduce or eliminate damage to the crop without substantially impairing the beneficial effect of the herbicide. For example, see U.S. Pat. Nos. 4,021,224 and 4,021,229 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist. As used herein, "antidote" describes, i.e., the continued effect of establishing herbicidal selectivity of herbicidal phytotoxicity to weed species and reduced or nonphytotoxicity to cultivated crop species.

As an alternative mode of action, the compounds of this invention may interfere with the normal herbicidal action of the thiolcarbamate-type herbicides to render them selective in their action. Whichever mode of action is present, the corresponding beneficial and desirable effect is the continued herbicidal effect of the thiolcarbamate with the accompanying decreased herbicidal effect on desired crop species. This advantage and utility will become more apparent hereinafter.

Therefore, the terms "herbicide antidotes" or "antidotal amount" is meant to describe that effect or the amount which produces the effect which tends to counteract the normal injurious herbicidal response that the herbicide might otherwise produce. Whether it is to be termed a remedy, interferent, protectant, or the like, will depend upon the exact mode of action. The mode of action is varied, but the effect, which is desirable, is the result of the method of treating the soil in which a crop is planted.

Thiolcarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, the beneficial use of the thiolcarbamate can be enhanced by the addition of an antidote compound.

DESCRIPTION OF THE INVENTION

It has been discovered that hydroxyacetyl oxazolidine compounds are effective antidotes for the protection of corn from thiolcarbamate herbicide injuries.

Hydroxyacetyl oxazolidine compounds have the following formula

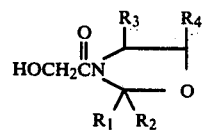

in which $R_1$-$R_4$ are each independently selected from the group consisting of hydrogen and alkyl having 1–4 carbon atoms.

In its preferred embodiment, the compound of this invention is 2,2,5-trimethyl-3-hydroxyacetyl oxazolidine of the formula

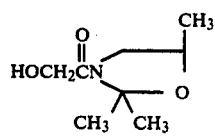

This invention also includes a two-part herbicidal system comprised of (a) a non-phytotoxic antidotally effective amount of a compound of the formula

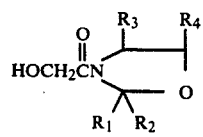

in which $R_1$-$R_4$ are each independently selected from the group consisting of hydrogen and alkyl having 1–4 carbon atoms; and (b) a herbicidal effective amount of a thiolcarbamate of the formula

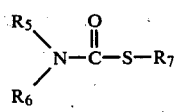

in which

R$_5$ is selected from the group consisting of alkyl having 1–6 carbon atoms and alkenyl having 2–6 carbon atoms;

R$_6$ is selected from the group consisting of alkyl having 1–6 carbon atoms, alkenyl having 2–6 carbon atoms, cyclohexyl and phenyl; or R$_5$ and R$_6$ together form an alkylene group having 5–10 carbon atoms; and R$_7$ is selected from the group consisting of alkyl having 1–6 carbon atoms, haloalkyl having 1–4 carbon atoms, cycloalkyl having 5–10 carbon atoms, phenyl, substituted phenyl, wherein the substituents are alkyl having 1–4 carbon atoms, haloalkyl having 1–4 carbon atoms, and halo, benzyl, and substituted benzyl, wherein the substituents are alkyl having 1–4 carbon atoms, haloalkyl having 1–4 carbon atoms, and halo.

The terms "alkyl" and "alkenyl" as used herein are intended to include both straight- and branched-chain groups. The term "halo" is intended to include mono- and polyhalo groups and includes, chloro, bromo, iodo, fluoro and mixtures thereof. All carbon atom ranges are intended to be inclusive of both upper and lower limits. Exemplary of "alkyl" are methyl, ethyl, n-propyl, isopropyl, n-butyl, isobutyl, tertiary butyl, pentyl, hexyl, and the like. Exemplary of "alkenyl" are such groups as vinyl, proenyl, butenyl, pentyl, hexenyl, and the like. Exemplary of cycloalkyl are cyclopentyl, cyclohexyl, 2,2 dimethyl cyclohexyl, cycloheptyl, and the like.

By way of exemplification, the active thiolcarbamate herbicides employed in the invention may include the following: EPTC, S-ethyl diisobutyl thiolcarbamate, S-propyl dipropyl thiolcarbamate, S-2,3,3-trichloroallyldiisopropyl thiolcarbamate, S-ethyl cyclohexyl ethyl thiolcarbamate, S-ethyl hexahydro-1H-azepine-1-carbothioate, S-4-chlorobenzyl diethyl thiolcarbamate, and combinations thereof.

This invention also includes the method of protecting crops from herbicidal injury which comprises applying to the locus where protection is desired an antidotally effective amount of a compound of the formula

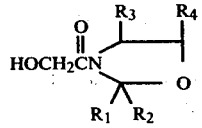

in which R$_1$–R$_4$ are each independently selected from the group consisting of hydrogen and alkyl having 1–4 carbon atoms.

Preparation

The thiolcarbamates of the present compositions can be prepared by the procedures described in U.S. Pat. Nos. 2,913,327, 2,983,747, 3,133,947, 3,185,720 and 3,198,786.

The preparation of the compounds of this invention utilize the 3-haloacyl oxazolidines as intermediates. These compounds are described in U.S. Pat. No. 3,959,304. The appropriate 3-haloacyl oxazolidines is treated with sodium formate and sodium carbonate in the presence of tetrabutyl phosphonium bromide. Work-up, purification and isolation of the compound involved standard procedures as will be illustrated by the following example. The following example more particularly illustrates the preparation of the present compounds.

EXAMPLE

Preparation of Intermediate 2,2,5-Trimethyl-3-Dichloroacetyl Oxazolidine

Eighteen milliliters (ml.) of a benzene solution containing 4.6 grams (g.) of 2,2,5-trimethyl oxazolidine was added to 25 ml. of benzene and 4.5 g. of triethylamine. Five and nine-tenths g. of dichloroacetyl chloride was added dropwise with stirring and cooling in an ice bath. When reaction was complete, the mixture was poured into water and the benzene layer separated, dried over anhydrous magnesium sulfate and the benzene removed under vacuum. Yield was 7.7 g. of an oil, $n_D^{30}$32 1.4950.

Preparation of 2,2,5-Trimethyl-3-Hydroxyacetyl-1,3-Oxazolidine

Thirty-eight and three tenths g. of 2,2,5-trimethyl-3-chloroacetyl-1,3-oxazolidine, 15.6 g. of sodium formate, 24.4 g. sodium carbonate and 1 g. of tetrabutyl phosphonium bromide were combined in 100 ml. of water and allowed to stir for four days. The mixture was heated to reflux for two hours, cooled and extracted with 50 ml. of methylene chloride. The inorganic salts were filtered off and the aqueous phase extracted three times with 25 ml. portions of methylene chloride. The combined methylene chloride extracts were washed with water, dried over anhydrous magnesium sulfate and stripped under vacuum. Yield was 30.9 g. of product, m.p. 50°–53° C. The structure was confirmed by infrared, nuclear magnetic resonance and mass spectroscopy.

Testing

Stock solutions of the herbicides were prepared by diluting the requisite amount of each herbicide in water. The solution compositions and application rates are summarized in Table I.

TABLE I

| | Herbicide Stock Solutions | | | |
| | Composition | | Application | |
| Herbicide Name | Herbicide (mg) | Water (ml) | ml/flat | lb/acre |
| --- | --- | --- | --- | --- |
| VERNAM® 6E S-propyl N,N-dipropyl thiolcarbamate | 2157 | 400 | 5 | 6.00 |
| EPTAM® 6E S-ethyl N,N-dipropyl thiolcarbamate | 2240 | 350 | 5 | 6.00 |

Stock solutions of each antidote compound were prepared at the desired concentrations by diluting the requisite amounts of each antidote in acetone. The compositions and rates for each method of application are summarized in Table II.

TABLE II

| Antidote Stock Solutions | | | | | |
| Antidote: 2,2,5-trimethyl-3-hydroxyacetyl oxazolidine | | | | | |
| Composition | | Application | | | |
| Antidote (mg) | Acetone (ml) | ml/flat | lb/acre | Method* | |
| --- | --- | --- | --- | --- | --- |
| 95 Stock A: | 15 | 1.50 | 5.00 | IF | |
| 60 | 15 | 5.00 | 5.00 | PPI | |
| 5 ml of A | 45 | 5.00 | 0.50 | PPI | |

TABLE II-continued

Antidote Stock Solutions
Antidote: 2,2,5-trimethyl-3-hydroxyacetyl oxazolidine

| Composition | | Application | | |
|---|---|---|---|---|
| Antidote (mg) | Acetone (ml) | ml/flat | lb/acre | Method* |
| Stock B: | | | | |
| 50 | 100 | | | |
| Dilution: | | | | |
| 10 ml of B | 90 | 4.00 | 0.05 | PPI |

*IF = In-furrow surface application.
PPI = Pre-plant incorporation of herbicide and antidote.

All of the soil used in the tests described herein was loamy sand soil treated with 50 parts per million (ppm) each of a commercially available fungicide, N-[tri-chloromethyl)-thio]-4-cyclohexene-1,2-dicarboximide, and 18-18-18 fertilizer, which contains 18% by weight equivalent each of nitrogen, phosphorus pentoxide, and potassium oxide.

The herbicides were applied to the soil be pre-plant incorporation (PPI). The antidote was applied by (PPI) and in-furrow (IF).

For (IF) antidote applications, a one pint (473 cubic centimeter) sample of soil from each planting flat was removed and retained. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

All flats were placed on greenhouse benches where temperature was maintained between 70° and 90° F. (21.1° to 32.2° C.). The flats were watered by sprinkling as needed to assure good plant growth.

Control flats contained the crop treated with herbicides only at the various rates.

Injury ratings were taken four weeks after application of the antidote. The effectiveness of the antidote was determined by visual comparison of injuries to the crop and weeds in the control and test flats to those in untreated flats.

The treated crop screened for diminution of herbicidal injury was corn (Zea Maize). The herbicide and antidote compositions were then screened on the weed species watergrass (*Echinochloa crusgalli*), and foxtail (*Setaria viridis*).

When 2,2,5-trimethyl-3-hydroxyacetyl oxazolidine was applied in furrow at 5 lb/A with VERNAM ® in the soil pre-plant incorporated at 6 lb/A, the crop, corn, after four weeks, gave a result of 0/90. That is, the antidotally untreated soil produced 90 percent injury to the corn, while the antidotally treated soil gave 100 percent protection with no injury to the corn plants. When the compound was applied pre-plant incorporated with EPTAM ® at 0.50 lb/A and 5 lb/A for the antidote and 6 lb/A for the herbicide with corn, the results were 20/75 and 0/75, respectively. That is, at 0.50 lb/A of antidote and 6 lb/A of EPTAM ® injury to corn was reduced from 75 percent to 20 percent; and at 5 lb/A of antidote and 6 lb/A of EPTAM ® injury to corn was reduced from 25 percent to 0 percent. These were four week ratings.

TABLE III

| 2,2,5-trimethyl-3-hydroxyacetyl oxazolidine | | Herbicidal Effectiveness | | % Weed Injury | | | |
|---|---|---|---|---|---|---|---|
| | | Herbicide | | Water-grass | | Foxtail | |
| Rate | Method | Name | Rate | U | T | U | T |
| 0.05 | PPI | EPTAM | 6.00 | 100 | — | 100 | — |
| 0.05 | PPI | EPTAM | 6.00 | 100 | — | 100 | — |
| 0.50 | PPI | EPTAM | 6.00 | 100 | — | 100 | — |
| 5.00 | PPI | EPTAM | 6.00 | 100 | — | 100 | — |

Formulations

The object of the formulation is to apply the compositions to the locus where control is desired by a convenient method. The "locus" may include soil, seeds, seedlings and vegetation.

The amount of antidote compound which comprises part of a herbicidal composition will generally range from approximately 0.001 to 30 parts by weight per weight of the herbicidal compound.

Formulations will generally contain several additives. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may also be included. Aids to rooting and growth, e.g., compost, manure, humus, sand, etc., may likewise be included. The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alochols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc. N.Y., 1973) at pages 79–84.

Granules comprise the herbicidal composition impregnated on a particulate inert carrier having a particle size of about 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use, the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging or mixing.

I claim:

1. A compound of the formula

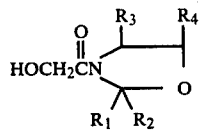

in which $R_1$–$R_4$ are each independently selected from the group consisting of hydrogen and alkyl having 1–4 carbon atoms.

2. A compound according to claim 1 in which $R_1$, $R_2$ and $R_4$ are each menthyl and $R_3$ is hydrogen.